United States Patent [19]

Montanio

[11] 4,179,814
[45] Dec. 25, 1979

[54] TOOTH CLEANING DEVICE

[76] Inventor: Louis P. Montanio, 2503 Prairie Creek Dr., Richardson, Tex. 75080

[21] Appl. No.: 866,759

[22] Filed: Jan. 3, 1978

[51] Int. Cl.$^2$ ................................................. A61C 1/08
[52] U.S. Cl. .......................................... 433/99; 15/23; 433/131
[58] Field of Search ............... 15/23, 3.53; 32/40, 32/26, 27

[56] References Cited

U.S. PATENT DOCUMENTS

| 2,185,229 | 1/1940 | Scott | 15/23 UX |
| 2,210,094 | 8/1940 | Mueller | 15/23 |
| 3,183,891 | 5/1965 | MacDonald | 15/3.53 |

Primary Examiner—Robert Peshock
Attorney, Agent, or Firm—Arnold, White & Durkee

[57] ABSTRACT

There is disclosed a tooth cleaning device especially designed and adapted for home use by the general public. The device employs an electric motor coupled by a direct gear drive to a shaft to which may be attached a variety of cleaning, polishing and massaging tips. The housing of the device is shaped to fit in the palm of the hand and is provided with an easily accessible switch. The device is so designed that it cannot be used to reach areas of the teeth and gums that must be treated professionally.

4 Claims, 3 Drawing Figures

TOOTH CLEANING DEVICE

BACKGROUND AND SUMMARY OF THE INVENTION

My invention relates to a tooth cleaning device for home use, powered by an electric motor and designed so that the device may be used safely by members of the general public.

From my experience as a practicing dentist, I have observed that there is a need for a device, available to the general public, that is easy to handle and to control for the purpose of removing surface stains and plaque from the facial surfaces of teeth. Such a device should not be suitable for reaching those areas of the teeth and gums where heavy tartar (calculus) formations may have accumulated. Such areas should be cleaned professionally by either a dentist or a dental hygienist during regular office visits.

The prior art is replete with devices which are suitable for use by trained professionals, such as U.S. Pat. Nos. 3,098,299 and 3,195,537, but none of these devices is suitable for use by untrained members of the general public.

I have invented a portable hand-held dental cleaning device having a substantially spheroidal housing shaped to fit the palm of the human hand. On the housing is mounted a substantially frusto-conical protective shield which is removably mounted on the housing, so that it may be removed from the housing for cleaning after the device has been used. The shield has an aperture approximately in the center of the frustum surface whose axis is approximately centrally located with respect to the housing and is substantially perpendicular to the portion of the housing which contacts the hand of the user when it is held. The device is powered by an electric motor. The axis of the rotatable shaft of the electric motor may be parallel to and spaced from the axis of the aperture of the protective shield. On the rotatable shaft of the electric motor is mounted a primary gear, which engages the geared portion of a central geared shaft disposed inside said housing. The central geared shaft extends from within the housing through the aperture of the protective shield, and is aligned such that the axis of the central shaft and the axis of the aperture in the protective shield substantially coincide. On the end of the central geared shaft distal from the housing is mounted a suitable tip for use in tooth cleaning and polishing and massaging of the gums.

My invention generally provides a novel approach to a quality dental hygiene program that may be carried on by members of the general public at home. My invention makes available a simple, inexpensive apparatus useful in the removal of tooth film without the risk of injury to the user.

One feature of my invention is the design of the housing of the device permitting the user to hold it in the palm like a bar of soap.

Another feature of this invention is the simplicity of a compact power source driving a small electric motor mounted within the hand-held unit, and completely insulated to eliminate any shock hazard.

My invention also features a readily removable protective shield which keeps saliva and polishing material from damaging the inner workings of the device.

A further feature of my invention is the location of the switch on the housing of the device to provide easy switch access to both right and left-handed people.

Yet another feature of my invention is the driving mechanism, which is entirely gear driven. This direct drive provides a reduction in rotational speed of the polishing tip for better control, while providing increased torque for more effective polishing. Greater maneuverability is also provided by the centrally located central gear shaft, which is located directly in line with the center of the palm of the hand, thus making it easier for the user to guide the unit over the areas of the teeth and gums to which the device is designed to be applied.

These features and other advantages of my invention will be apparent to persons skilled in this art from reading the specification and the claims appended hereto.

DETAILED DESCRIPTION OF THE PREFERRED EMBODIMENT

Figure 1:
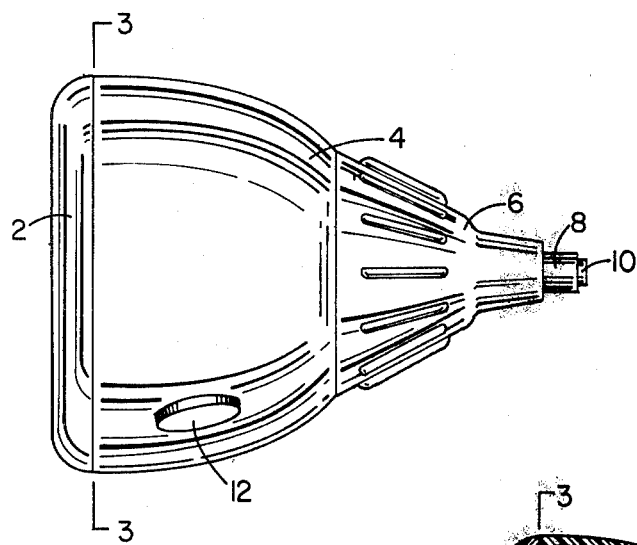
FIG. 1 is a side view of the outside of a preferred embodiment of my invention.

FIG. 1 shows a side view of the exterior of a device constructed in accordance with my invention. The housing is in two parts, a base portion 2 having a flat surface to fit the palm of a user's hand and an oblate portion 4. The housing may also be spheroidal in overall form, providing a rounded outer surface around which the user can comfortably close his hand and maintain a secure grip on the device. To the end of oblate portion 4 is mounted a substantially frusto-conical protective shield 6. The depicted shield has ribs on it to provide a gripping surface which facilitates unscrewing the shield 6 from the housing portion 4 for cleaning while the shield is still damp from use. The distal end 8 of the central geared shaft of the device (shown in greater detail in FIG. 2) extends from inside the shield 6 through an aperture in the frustum end of the shield. Threaded connector 10 is mounted within the distal end 8 of the central geared shaft. The user may attach various dental tips (not depicted) to the device by screwing them into the threaded connector 10. Among the tips I consider suitable for use with the device are the well-known and time-proven rubber polishing cup or the newer plastic cup demonstrated to be less abrasive than the rubber cup in studies done at Indiana University. Ordinary household tooth paste can be used as the polishing agent, but for stubborn stains and plaque a compound of fine grit flour of pumice and glycerin may be used. I recommend only occasional use of the pumice compound because of its greater abrasiveness.

Figure 2:
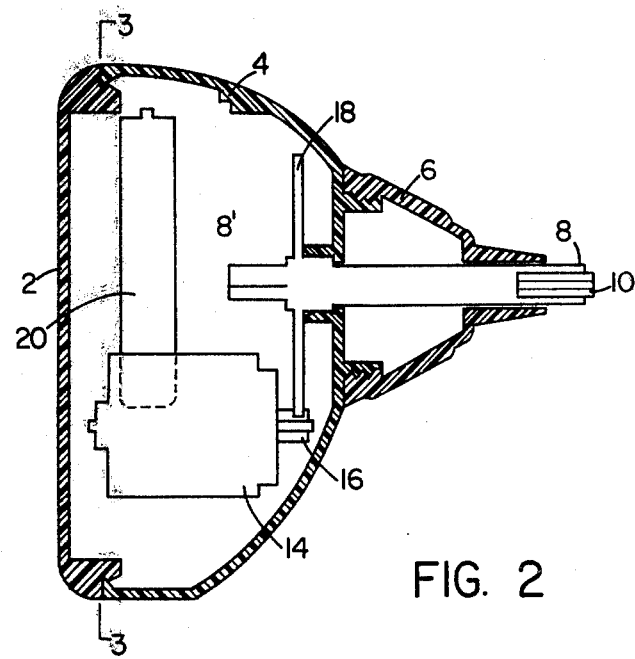
FIG. 2 is a schematic longitudinal cross section of the device depicted in FIG. 1.

FIG. 2 shows the internal construction of my device schematically. Connecting wires and structural supporting elements within the housing, all of which are conventional, have been omitted from FIGS. 2 and 3 to make comprehension of the drawings easier. The protective shield 6 is shown to be mounted on oblate portion 4 by threads, thus permitting easy removal of the shield for cleaning after each use of the device. The shield 6 protects the housing and internal parts thereof from spattering of saliva and polishing material. The shield also stabilizes the central geared shaft 8. An electric motor 14 is mounted within the housing. On the end of the rotatable shaft of the motor is a primary gear 16. This primary gear 16 is shown to be directly engaged to geared disk 18, which may be either attached to or integral with the central shaft 8. The end of the central geared shaft proximal to the hand of the user when the device is in operation is denoted 8'. FIG. 2 also depicts one of the non-rechargeable dry cell batteries 20 in its appoximate position within the device.

Figure 3:
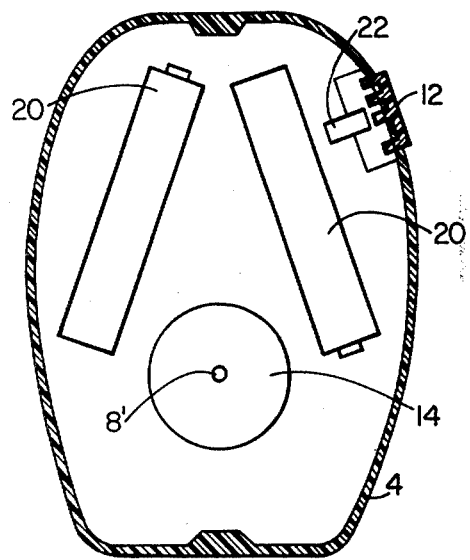
FIG. 3 is a schematic view of the interior of the device of FIG. 1 opened along section 3—3.

FIG. 3 more clearly shows the location of the batteries 20 in the housing with relation to electric motor 14 and the mounting of contact switch button 12 (also shown on FIG. 1) and plunger 22 on the oblate housing portion 4. The electric motor is energized by depressing the switch button 12 and thus completing the circuit between the batteries 20 and the electric motor 14. As depicted, the switch button 12 is within easy reach of the thumb of the left hand or the index finger of the right hand when the device is picked up by the user. The location of the switch button on a quadrant of the curved surface of the housing portion 4 insures easy switch access while allowing the user to maintain a firm and confortable grip on the device.

The housing and the internal parts of the device (except for the motor, connecting wires, battery holders and the internal parts of the contact switch) are preferably constructed of plastic for light weight. I have found that the best results are obtained by using a three-volt motor which turns at between about 800 and about 1200 r.p.m. Since the device is intended for easy home use and thus should be cordless, the power source is preferably two 1½ volt penlight non-rechargeable dry cell batteries. The number of teeth on the primary gear 16 and the gear disk 18 and the diameters of each are chosen to yield preferably about an 8 to 1 speed reduction from the motor to the central geared shaft. This reduction provides increased polishing torque while allowing the user greater control over the mouth areas to which he wishes to apply the rotating polishing or massaging tip. Belt drives do not provide the simultaneous increased torque with speed reduction that my invention requires.

The direct gear drive also provides control advantages not directly related to speed. As shown in the drawings, my preferred embodiment employs a rotating central gear shaft which is oriented to be substantially perpendicular to the palm of the user's hand and to be parallel to but spaced from the rotating shaft of the electric motor. This configuration produces a balanced device in which the rotation of the central shaft, and thus of the polishing tip, is in line with the axis of greatest ease of motor control of the human hand. I have found that it is much easier and safer for untrained persons to guide a polishing device through the palm of the hand than it is for them to guide a polishing device which is held in the fingers alone. The central shaft location also provides another feature of my invention, which is that untrained users of the device cannot easily get access to those areas of the mouth where tartar tends to form. People using the device will, of course, be looking into a mirror as they guide the tip and will thus not be able to see around the housing of the device to get at those areas requiring professional care. Safety is also enhanced by the knowledge of the general public deriving from their experiences in dental offices that applying excessive pressure may cause pain. It must be remembered that my invention is not a professional dental appliance and is intended for cosmetic cleaning only.

The foregoing description of the invention has been directed to a particular embodiment in accordance with the requirements of the Patent Act and for purposes of explanation and illustration. It will be apparent, however, to those skilled in the art that many modifications and changes may be made without departing from the scope and spirit of my invention. For example, a person skilled in the art will be able to use my disclosure to construct devices in accordance with my invention for applications not specifically disclosed herein. Modifications in the device disclosed necessary to satisfy the particular needs of any given environment or in constructing the device of materials especially chosen for environmental stability or unusual strength are well within the state of the art. These and other modifications of my invention will be apparent to those skilled in the art. It is my intention in the following claims to cover all such equivalent modifications and variations as fall within the true scope and spirit of my invention.

What is claimed is:

1. A portable hand-held dental cleaning device, comprising:
    a housing adapted to fit the palm of the human hand and including a substantially flat back surface to fit adjacent a user's palm, with the flat surface blending into rounded top and side surfaces forming a generally oblate portion around which a user's fingers may fit for gripping;
    a substantially frusto-conical protective shield removably mounted on the front of said housing such that said curved surfaces slope toward said shield, which includes an aperture whose axis is approximately central to said housing and substantially perpendicular to the portion of said back housing surface;
    an electric motor means disposed within said housing and including a rotatable output shaft parallel to and spaced from the axis of the aperture of the protective shield;
    a primary gear on the rotatable shaft of said electric motor;
    a central geared shaft disposed in said housing and extending through the aperture of said protective shield such that the axis of said central geared shaft and the axis of said aperture substantially coincide, wherein said central geared shaft directly engages said primary gear;
    a depressible switch for selectively activating the electric motor and being mounted on one of the rounded side surfaces adjacent the top rounded surface in a position so that the switch is accessible for use with either hand by either the thumb on one hand or the index finger on the other hand; and
    the end of said spaced shaft which extends outwardly of the housing including a connection for receiving a suitable tip for dental use.

2. The device of claim 1 wherein the power source for the electric motor is at least one non-rechargeable dry cell battery.

3. The device of claim 2 wherein the gear ratio between the primary gear and the central geared shaft is approximately 8 to 1.

4. The device of claim 3 wherein the electric motor means rotates the output shaft at between about 800 and about 1200 r.p.m.

* * * * *